(12) United States Patent
Piergallini et al.

(10) Patent No.: US 9,603,929 B2
(45) Date of Patent: *Mar. 28, 2017

(54) COMBINATION OF AN OXIDANT, A PHOTOSENSITIZER AND A WOUND HEALING AGENT FOR ORAL DISINFECTON AND TREATMENT OF ORAL DISEASE

(71) Applicant: KLOX Technologies Inc., Laval (CA)

(72) Inventors: Remigio Piergallini, Grottammare Ascoli Piceno (IT); Nikolaos Loupis, Athens (GR)

(73) Assignee: KLOX Technologies Inc., Laval (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/539,310

(22) Filed: Nov. 12, 2014

(65) Prior Publication Data

US 2015/0290320 A1  Oct. 15, 2015

Related U.S. Application Data

(63) Continuation of application No. 14/137,666, filed on Dec. 20, 2013, now Pat. No. 8,986,746, which is a continuation of application No. 13/387,328, filed as application No. PCT/CA2010/001134 on Jul. 19, 2010, now Pat. No. 8,685,466.

(60) Provisional application No. 61/226,354, filed on Jul. 17, 2009.

(51) Int. Cl.

| | |
|---|---|
| *A61K 33/40* | (2006.01) |
| *A61K 41/00* | (2006.01) |
| *A61K 31/4166* | (2006.01) |
| *A61K 31/7008* | (2006.01) |
| *A61K 31/728* | (2006.01) |
| *A61K 45/06* | (2006.01) |
| *A61K 31/327* | (2006.01) |
| *A61K 8/38* | (2006.01) |
| *A61K 8/49* | (2006.01) |
| *A61K 8/60* | (2006.01) |
| *A61K 8/73* | (2006.01) |
| *A61K 8/97* | (2006.01) |
| *A61N 5/06* | (2006.01) |
| *A61Q 11/00* | (2006.01) |
| *A61Q 17/00* | (2006.01) |

(52) U.S. Cl.
CPC .............. *A61K 41/008* (2013.01); *A61K 8/38* (2013.01); *A61K 8/494* (2013.01); *A61K 8/498* (2013.01); *A61K 8/602* (2013.01); *A61K 8/735* (2013.01); *A61K 8/97* (2013.01); *A61K 31/327* (2013.01); *A61K 31/4166* (2013.01); *A61K 31/7008* (2013.01); *A61K 31/728* (2013.01); *A61K 33/40* (2013.01); *A61K 41/0038* (2013.01); *A61K 41/0042* (2013.01); *A61K 41/0057* (2013.01); *A61K 45/06* (2013.01); *A61N 5/062* (2013.01); *A61N 5/0624* (2013.01); *A61Q 11/00* (2013.01); *A61Q 17/005* (2013.01); *A61N 2005/0606* (2013.01)

(58) Field of Classification Search
None
See application file for complete search history.

(56) References Cited

U.S. PATENT DOCUMENTS

| 2,877,221 A | 3/1959 | Lanbach |
|---|---|---|
| 3,293,127 A | 12/1966 | Beck |
| 3,309,274 A | 3/1967 | Brilliant |
| 3,372,125 A | 3/1968 | Hill |
| 3,595,798 A | 7/1971 | Smith et al. |
| 3,597,362 A | 8/1971 | Rauhut et al. |
| 3,652,420 A | 3/1972 | Hill |
| 3,671,450 A | 6/1972 | Rauhut et al. |
| 3,728,446 A | 4/1973 | Roberts et al. |
| 4,574,097 A | 3/1986 | Honeycutt |
| 4,846,165 A | 7/1989 | Hare et al. |
| 4,891,211 A | 1/1990 | Winston |
| 4,992,256 A | 2/1991 | Skaggs et al. |
| 5,658,148 A | 8/1997 | Neuberger et al. |
| 5,749,968 A | 5/1998 | Melanson et al. |
| 5,785,527 A | 7/1998 | Jensen et al. |
| 5,844,016 A | 12/1998 | Sawhney et al. |
| 5,858,332 A | 1/1999 | Jensen et al. |
| 5,922,331 A | 7/1999 | Mausner |
| 5,977,199 A | 11/1999 | Xie |

(Continued)

FOREIGN PATENT DOCUMENTS

| CA | 2 222 027 A1 | 6/1998 |
|---|---|---|
| CA | 2 360 202 A1 | 7/2000 |

(Continued)

OTHER PUBLICATIONS

"Resources: Fluorochrome Absorption Emission Wavelengths" [Online] XP002449595 Retrieved from the Internet: URL: http://www.sciencegateway.org/resource s/fae1.htm>[retrieved on Sep. 6, 2007] see p. 2: Rhodamine WT emission nm 555 p. 2.
Alster et al., "Photodynamic therapy: practical cosmetic applications," Journal of Drugs in Dermatology, vol. 5(8); pp. 764-768 XP008147410 (2006).
Antunes et al., "Evaluation of the clastogenicity and anticlastongenicity of the carotenoid bixin in human lymphocyte cultures," Mutat Res. 585(1-2):113-9 (2005).
Berneburg et al., "Phototherapy with Narrowband UVB," Acta Derm Venereol, 85(1-11) (2005).
Colman and Roenigk, "The healing of wounds in the skin of piglets treated with benzoyl peroxide,"The Journal of Dermatologic Surgery and Oncology, vol. 4(9), pp. 705-707 (1978). XP 009151883.
Darzynkiewicz e al., "Photosensitizing effects of the tricyclic heteroaromatic cationic dyes pyronin Y and toluidine blue O (tolonium chloride)," Cancer Res., 48(5) 1295-9 (1988).
De et al., "Environmental effects on the aggregation of some xanthene dyes used in lasers," Spectrochim Acta A Mol Biomol Spectrosc., 61(8) 1821-33 (2005).

(Continued)

Primary Examiner — Hasan Ahmed
(74) Attorney, Agent, or Firm — Ropes & Gray LLP (57) ABSTRACT

The present document describes methods of use of photo activated compositions for oral disinfection and/or treatments which comprise at least one oxidant, at least one photoactivator capable of activating the oxidant, and at least one healing factor chosen from hyaluronic acid, glucosamine and allantoin, in association with a pharmacologically acceptable carrier.

20 Claims, 5 Drawing Sheets

(56) References Cited

U.S. PATENT DOCUMENTS

| | | |
|---|---|---|
| 6,030,222 A | 2/2000 | Tarver |
| 6,036,493 A | 3/2000 | Sharma |
| 6,056,548 A | 5/2000 | Neuberger et al. |
| 6,084,005 A | 7/2000 | Fukunishi et al. |
| 6,107,466 A | 8/2000 | Hasan et al. |
| 6,121,341 A | 9/2000 | Sawhney et al. |
| 6,149,895 A | 11/2000 | Kutsch |
| 6,162,055 A | 12/2000 | Montgomery et al. |
| 6,254,388 B1 | 7/2001 | Yarborough |
| 6,267,976 B1 | 7/2001 | Barnhart et al. |
| 6,337,357 B1 | 1/2002 | Fukunishi et al. |
| 6,343,933 B1 | 2/2002 | Montgomery et al. |
| 6,361,329 B1 | 3/2002 | Dekker et al. |
| 6,365,134 B1 | 4/2002 | Orlowski et al. |
| 6,387,353 B1 | 5/2002 | Jensen et al. |
| 6,391,283 B1 | 5/2002 | Jensen et al. |
| 6,420,455 B1 | 7/2002 | Landgrebe et al. |
| 6,423,697 B1 | 7/2002 | Friedman |
| 6,440,396 B1 | 8/2002 | McLaughlin |
| 6,444,725 B1 | 9/2002 | Trom et al. |
| 6,475,497 B1 | 11/2002 | Rajaiah et al. |
| 6,485,709 B2 | 11/2002 | Banerjee et al. |
| 6,488,914 B2 | 12/2002 | Montgomery |
| 6,514,543 B2 | 2/2003 | Montgomery |
| 6,528,555 B1 | 3/2003 | Nikutowski et al. |
| 6,536,628 B2 | 3/2003 | Montgomery |
| 6,541,460 B2 | 4/2003 | Petito |
| 6,558,653 B2 | 5/2003 | Andersen et al. |
| 6,846,182 B1 | 1/2005 | Sibner |
| 6,905,672 B2 | 6/2005 | Rajaiah et al. |
| 6,960,079 B2 | 11/2005 | Brennan et al. |
| 7,066,941 B2 | 6/2006 | Perricone |
| 7,081,128 B2 | 7/2006 | Hart et al. |
| 7,114,953 B1 | 10/2006 | Wagner |
| 7,220,438 B2 | 5/2007 | Quintanilla Almagro et al. |
| 7,314,470 B2 | 1/2008 | Malodobry |
| 7,354,448 B2 | 4/2008 | Altshuler et al. |
| 8,075,875 B2 | 12/2011 | Piergallini et al. |
| 8,182,473 B2 | 5/2012 | Altshuler et al. |
| 8,632,822 B2 | 1/2014 | Piergallini et al. |
| 8,637,086 B2 | 1/2014 | Piergallini et al. |
| 8,658,219 B2 | 2/2014 | Piergallini et al. |
| 8,685,466 B2 | 4/2014 | Piergallini et al. |
| 8,911,791 B2 | 12/2014 | Piergallini et al. |
| 8,974,833 B2 * | 3/2015 | Piergallini et al. ........... 424/616 |
| 8,986,719 B2 | 3/2015 | Piergallini et al. |
| 8,986,745 B2 * | 3/2015 | Piergallini et al. ........... 424/616 |
| 8,986,746 B2 * | 3/2015 | Piergallini et al. ........... 424/616 |
| 2001/0022970 A1 | 9/2001 | Dees et al. |
| 2003/0133940 A1 | 7/2003 | Dees et al. |
| 2003/0198605 A1 | 10/2003 | Montgomery |
| 2004/0026569 A1 | 2/2004 | Preston |
| 2004/0136971 A1 | 7/2004 | Scharp et al. |
| 2004/0191330 A1 | 9/2004 | Keefe et al. |
| 2005/0020696 A1 | 1/2005 | Montgomery et al. |
| 2005/0026298 A1 | 2/2005 | Bickett et al. |
| 2005/0049228 A1 | 3/2005 | Albrecht et al. |
| 2005/0059731 A1 | 3/2005 | Albrecht et al. |
| 2005/0098766 A1 | 5/2005 | Watson et al. |
| 2005/0123588 A1 | 6/2005 | Zhu et al. |
| 2006/0099155 A1 | 5/2006 | MacDonald et al. |
| 2006/0198796 A1 | 9/2006 | Giniger et al. |
| 2006/0287211 A1 | 12/2006 | Barbizan et al. |
| 2007/0092469 A1 | 4/2007 | Jacobs |
| 2007/0128132 A1 | 6/2007 | Piergallini et al. |
| 2007/0166369 A1 | 7/2007 | Neuberger et al. |
| 2007/0191249 A1 | 8/2007 | Lant |
| 2007/0244195 A1 | 10/2007 | Burkhart et al. |
| 2008/0058689 A1 | 3/2008 | Holloway et al. |
| 2008/0108681 A1 | 5/2008 | Scimeca et al. |
| 2008/0113037 A1 | 5/2008 | Green et al. |
| 2008/0206159 A1 | 8/2008 | Tamarkin et al. |
| 2008/0255498 A1 | 10/2008 | Houle |
| 2008/0305101 A1 | 12/2008 | Ruoslahti et al. |
| 2010/0266989 A1 | 10/2010 | Piergallini et al. |
| 2011/0218482 A1 | 9/2011 | Piergallini et al. |
| 2011/0224599 A1 | 9/2011 | Piergallini et al. |
| 2014/0303547 A1 | 10/2014 | Loupis et al. |

FOREIGN PATENT DOCUMENTS

| | | |
|---|---|---|
| CA | 2 457 590 A1 | 3/2003 |
| CA | 2 551 613 | 12/2005 |
| CA | 2 580 381 A1 | 1/2006 |
| CA | 2 809 405 A1 | 1/2012 |
| EP | 0356868 | 3/1990 |
| EP | 0 380 157 A1 | 8/1990 |
| EP | 0 704 539 A2 | 4/1996 |
| EP | 1 235 543 A1 | 9/2002 |
| EP | 1 235 544 A1 | 9/2002 |
| EP | 1 749 532 A1 | 2/2007 |
| EP | 1 779 891 A1 | 5/2007 |
| EP | 1 951 184 | 8/2008 |
| EP | 2 338 465 | 6/2011 |
| JP | H092925 | 1/1977 |
| JP | 01-279838 | 11/1989 |
| JP | 02-233612 | 9/1990 |
| JP | 03-169805 | 7/1991 |
| JP | 10-182390 A | 7/1998 |
| JP | 10-330235 | 12/1998 |
| JP | 2000-053550 | 2/2000 |
| JP | 2001-511137 A | 8/2001 |
| JP | 2002-502864 | 1/2002 |
| JP | 2002-226349 A | 8/2002 |
| JP | 2002-293747 A | 10/2002 |
| JP | 2003-339875 A | 12/2003 |
| JP | 04-219756 B2 | 2/2009 |
| WO | WO-81/00513 A1 | 3/1981 |
| WO | WO-90/09779 A1 | 9/1990 |
| WO | WO-91/02530 A1 | 3/1991 |
| WO | WO-97/21420 | 6/1997 |
| WO | WO-98/10738 | 3/1998 |
| WO | WO-98/11827 | 3/1998 |
| WO | WO-98/23219 | 6/1998 |
| WO | WO-98/30169 | 7/1998 |
| WO | WO-98/33761 A1 | 8/1998 |
| WO | WO-9836700 | 8/1998 |
| WO | WO-99/39238 A1 | 8/1999 |
| WO | WO-99/40870 A1 | 8/1999 |
| WO | WO-99/49823 | 10/1999 |
| WO | WO-99/63900 | 12/1999 |
| WO | WO-00/40266 A2 | 7/2000 |
| WO | WO-01/00190 A2 | 1/2001 |
| WO | WO-01/12181 A1 | 2/2001 |
| WO | WO-02/22097 | 3/2002 |
| WO | WO-0287642 | 11/2002 |
| WO | WO-03/000215 A1 | 1/2003 |
| WO | WO-03/017824 A2 | 3/2003 |
| WO | WO-03/061696 A2 | 7/2003 |
| WO | WO-03/099247 A1 | 12/2003 |
| WO | WO-2004/028498 | 4/2004 |
| WO | WO-2004/081222 A2 | 9/2004 |
| WO | WO-2004073540 | 9/2004 |
| WO | WO-2005/009604 A1 | 2/2005 |
| WO | WO-2005/051305 A2 | 6/2005 |
| WO | WO-2006/014597 A1 | 2/2006 |
| WO | WO-2006/032847 A1 | 3/2006 |
| WO | WO-2006/047868 A1 | 5/2006 |
| WO | WO-2006/072243 A1 | 7/2006 |
| WO | WO-2006/125650 A1 | 11/2006 |
| WO | WO-2006/135344 A1 | 12/2006 |
| WO | WO-2007/025244 A2 | 3/2007 |
| WO | WO-2007/080453 A2 | 7/2007 |
| WO | WO-2008/011707 A1 | 1/2008 |
| WO | WO-2008/013962 A2 | 1/2008 |
| WO | WO-2008052081 | 5/2008 |
| WO | WO-2008096182 | 8/2008 |
| WO | WO-2009/089346 A2 | 7/2009 |
| WO | WO-2010/051636 A1 | 5/2010 |
| WO | WO-2010/051641 A1 | 5/2010 |
| WO | WO-2011/006263 A1 | 1/2011 |
| WO | WO-2011/058448 A2 | 5/2011 |
| WO | WO-2011/134087 A1 | 11/2011 |

(56) References Cited

FOREIGN PATENT DOCUMENTS

| WO | WO-2012/011875 A1 | 1/2012 |
|----|-------------------|--------|
| WO | WO-2013/155620 A1 | 10/2013 |
| WO | WO-2014/040176 A1 | 3/2014 |

OTHER PUBLICATIONS

Decraene et al., "Cellulose Acetate Containing Toluidine Blue and Rose Bengal is an Effective Antimicrobial Coating when Exposed to White Light," Applied and Env. Microbiology, 72:6(4436-4439) (Jun. 2006).
FDA, Color Additive Status List: http://www.cfsanJda.gov/-dms/opa-appc.html.; FDA, Product Classification Database Search, Device: Eosin y: database updated Jun. 6, 2008.
Fischersci, :Material Safety Data Sheet: Sodium acetate buffer. https://fscimagef.fishersci.com/msds/91502.htm (Apr. 13, 2000).
Goldberg, David J., "Photodynamic therapy in skin rejuvenation," Clinics in Dermatology, vol. 26(6), pp. 608-613, XP025545890 (2008).
International Search Report (PCT/CA2010/001134) dated Oct. 8, 2010.
Jankowski et al., "The action of photosensitizers and serum in a bactericidal process. II. The effects of dyes: hypericin, eosin Y and saphranine O," Pol J Microbiol., 54(4):323-30 (2005).
Kelly et al., "Combined photodynamic and photothermal induced injury enhances damage to in vivo model blood vessels," Lasers in Surgery and Medicine, vol. 34(5); pp. 407-413, XP008147412 (2004).
McCullach et al. Photosensitized destruction of Chlorella vulgaris by methylene blue or nuclear fast red combined with hydrogen peroxide under visible light irradiation, Environ. Sci. Tech, vol. 40, pp. 2421-2425 (2006).
Meisel et al., "Photodynamic therapy for periodontal diseases: State of the art," Journal of Photochemistry and Photobiology B: Biology, 2005, 79, 159-170.
Montenegro et al., "Model studies on the photosensitized isomerication of bixin," J Agric Food Chem, 52(2): 367-73 (2004).

Nolan et al., "The efficacy of topical hyaluronic acid in the management of oral lichen planus," Journal of Oral Pathology and Medicine, 38:3, pp. 299-303 (Feb. 23, 2009), XP055103025.
Publication date of following document established by Internet Archive Wayback Machine<URL: http://web.archive.org/web/20090208211504/http://en.wikipedia.org/wiki/Eosin Aug. 2, 2009.
Rodgers, William, "Fluorescence Polarization Standards for High-Throughput Screening and Imaging," Bio Techniques, vol. 32, pp. 34-42 (2002).
Roy et al., "Dermal Wound Healing8 is Subject to Redox Control," Molecular Therapy, vol. 13(1), pp. 211-220 (2006). XP005197711.
Sezer et al., "Topical Drug Delivery Using Chitosan Nano- and Microparticles," *Informa* Uk, pp. 1129-1146, (ISSN 1742-5247 (2012).
Steinberg et al., "Genetic and Physiological Effects of Noncoherent Visible Light Combined with Hydrogen Peroxide on Streptococcus mutans in Biofilm," Antimicrobial Agents and Chemotherapy, 52:7, pp. 2626-2631, (Mar. 3, 2008) (XP055103315).
Subba et al, "Photocatalytic transformation of dyes and by-products in the presence of hydrogen peroxide," Environ Technol., 24(8) 1025-30 (2003).
Sun, Grace, "Lasers and Light Amplification in Dentistry," retrieved online at http://www.sundds.comllaser/ on Jun. 23, 2005.
Chen et al., "Study of the Chemiluminescent Characteristics of Some Xanthone Dyes," Analytica Chimica Acta, 292(1-2):159-167 (1994).
Mintel, "Teens Braces Cleaner," http://gnpd.com, Jan. 2004 (2 pages).
Nolan et al., "The Efficacy of Topical Hyaluronic Acid in the Management of Oral Lichen Planus," Journal of Oral Pathology and Medicine, 38(3):299-303 (2006).
Ariizumi et al., "Clinical Evaluation of a Topical Applicant TSG-88 for Periodontal Disease," Dental Drug Therapy, 10(2):157-168 (1991) (English Abstract included).
PCT International Search Report and Written Opinion for International U.S. Appl. No. PCT/GR2007/000006, dated Oct. 12, 2007 (8 pages).
PCT International Search Report and Written Opinion for International Serial No. PCT/IB2006/004034, dated Sep. 20, 2007 (13 pages).

\* cited by examiner

FIG. 5C

COMBINATION OF AN OXIDANT, A PHOTOSENSITIZER AND A WOUND HEALING AGENT FOR ORAL DISINFECTON AND TREATMENT OF ORAL DISEASE

RELATED APPLICATIONS

The application is a continuation of U.S. patent application Ser. No. 14/137,666, filed Dec. 20, 2013, which is a continuation of U.S. patent application Ser. No. 13/387,328, filed on Jun. 14, 2012 and now U.S. Pat. No. 8,685,466, which is a national stage filing under 35 U.S.C. §371 of International Application No. PCT/CA2010/001134, filed on Jul. 19, 2010, which claims the benefit of the filing date under 35 U.S.C. §119(e) to U.S. Provisional Application No. 61/226,354, filed on Jul. 17, 2009, the entire contents of which is hereby incorporated by reference. International Application No. PCT/CA2010/001134 was published under PCT Article 21(2) in English.

TECHNICAL FIELD

This description relates to the field of antibacterial periodontal composition and method of full mouth disinfection and photodynamic assisted periodontal treatment.

BACKGROUND OF THE INVENTION

The primary goal of periodontal treatment is to control the periodontal infection by altering or eliminating the microbial etiology and contributing factors.

To date, here is considerable evidence to support scaling and root planning (SRP) as one of the most effective procedures for the treatment of infectious periodontal diseases.

Treatment strategies used in periodontal treatment include full mouth disinfection although there is only a minor additive effect compared to conventional SRP.

There is general agreement that SRP in addition to improving clinical parameters reduces the microbial load and results in a shift toward a more health-compatible microflora.

However, there are conflicting reports about the ability of SRP to completely eradicate or suppress important periodontal pathogens.

SUMMARY OF THE INVENTION

In accordance with one embodiment, there is disclosed a use of a photoactivated composition for the manufacture of a medicament for oral disinfection and/or the treatment of an oral disease, the composition containing at least one oxidant, at least one photoactivator capable of activating the oxidant; and at least one healing factor chosen from hyaluronic acid, glucosamine and allantoin, in association with a pharmacologically acceptable carrier.

In accordance with one embodiment, there is disclosed a use of a photoactivated composition for oral disinfection, for the treatment of an oral disease, and favor healing of the disease, and/or for the treatment of periodontitis, the composition containing at least one oxidant; at least one photoactivator capable of activating the oxidant; and at least one healing factor chosen from hyaluronic acid, glucosamine and allantoin; in association with a pharmacologically acceptable carrier.

The oral disease may be chosen from gingivitis, periodontitis, periodontal disease, oral thrush, lichen planus, and stomatitis.

The oxidants may be chosen from hydrogen peroxide, carbamide peroxide, peroxy acid, alkali metal percarbonate and benzoyl peroxide. Preferred oxidants are hydrogen peroxide and carbamide peroxide, and combination thereof.

The antibacterial periodontal composition may further comprise at least one hydrophilic gelling agent.

The hydrophilic gelling agent may be chosen from glucose, modified starch, methyl cellulose, carboxymethyl cellulose, propyl cellulose, hydroxypropyl cellulose, Carbopol® polymers, alginic acid, sodium alginate, potassium alginate, ammonium alginate, calcium alginate, agar, carrageenan, locust bean gum, pectin, gelatin.

The photoactivators may be chosen from a xanthene derivative dye, an azo dye, a biological stain, and a carotenoid.

The xanthene derivative dye may be chosen from a fluorene dye, a fluorone dye, and a rhodole dye.

The fluorene dye may be chosen from a pyronine dye and a rhodamine dye.

The pyronine dye may be chosen from pyronine Y and pyronine B.

The rhodamine dye may be chosen from rhodamine B, rhodamine G and rhodamine WT.

The fluorone dye may be chosen from fluorescein and fluorescein derivatives.

The fluorescein derivative may be chosen from phloxine B, rose bengal, and merbromine.

The fluorescein derivative may be chosen from eosin Y, eosin B and erythrosine B. Preferably, the fluorescein derivative is eosin Y.

The azo dye may be chosen from methyl violet, neutral red, para red, amaranth, carmoisine, allura red AC, tartrazine, orange G, ponceau 4R, methyl red, and murexide-ammonium purpurate.

The biological stain may be chosen from saffranin O, basic fuchsin, acid fuschin, 3,3' dihexylocarbocyanine iodide, carminic acid, and indocyanine green.

The carotenoid may be chosen from crocetin, α-crocin (8,8-diapo-8,8-carotenoic acid), zeaxanthine, lycopene, α-carotene, β-carotene, bixin, and fucoxanthine.

The carotenoid may be present in the composition as a mixture chosen from saffron red powder, annatto extract and brown algae extract.

The antibacterial periodontal composition may further comprise at least one chelating agent.

The chelating agent may be chosen from ethylenediaminetetraacetic acid (EDTA) and ethylene glycol tetraacetic acid (EGTA).

In accordance with one embodiment, there is disclosed a method of full mouth disinfection and/or photodynamic assisted oral treatment of a patient which has the steps of:
  a) applying in a patient's mouth a composition containing at least one oxidant, at least one photoactivator capable of activating the oxidant; and at least one healing factor chosen from hyaluronic acid, glucosamine and allantoin; and
  b) treating said mouth of step a) to actinic light for a time sufficient for said photoactivator to cause activation of said oxidant.

The oral treatment may be for the treatment of an oral disease, and the disease may be gingivitis, periodontitis, periodontal disease, oral thrush, lichen planus, stomatitis, herpes simplex lesion, oral mucositis, oral ulcers, oral submucous fibrosis, and glossitis.

The method of full mouth disinfection and photodynamic assisted oral treatment may comprise exposing the mouth to actinic light for a period of less than about 5 minutes, or for a period of about 60 seconds to about 5 minutes.

The method of full mouth disinfection and photodynamic assisted oral treatment may comprise exposing the mouth to actinic light for a period of less than about 5 minutes, or for a period of about 60 seconds to about 5 minutes per cm$^2$ of an area to be treated.

The method of full mouth disinfection and photodynamic assisted oral treatment may comprise exposing the mouth to a source of actinic light that is over the area being treated.

The method of full mouth disinfection and photodynamic assisted oral disease treatment may comprise applying the composition on a gingiva, near at least one tooth, and on at least one tooth, and the at least one tooth is exposed to actinic light for a period of about at least 10 seconds on a vestibular side, and of about at least 10 seconds on a oral side.

The method of full mouth disinfection and photodynamic assisted oral treatment may comprise exposing the mouth to actinic light that may be visible light having a wavelength between about 400 nm and about 700 nm, or about 400 nm and about 600 nm and preferably about 450 nm and about 700 nm.

The oxidants may be chosen from hydrogen peroxide, carbamide peroxide and benzoyl peroxide.

The antibacterial periodontal composition may further comprise at least one hydrophilic gelling agent.

The hydrophilic gelling agent may be chosen from glucose, modified starch, methyl cellulose, carboxymethyl cellulose, propyl cellulose, hydroxypropyl cellulose, Carbopol® polymers, alginic acid, sodium alginate, potassium alginate, ammonium alginate, calcium alginate, agar, carrageenan, locust bean gum, pectin, gelatin.

The photoactivators may be chosen from a xanthene derivative dye, an azo dye, a biological stain, and a carotenoid.

The xanthene derivative dye may be chosen from a fluorene dye, a fluorone dye, and a rhodole dye.

The fluorene dye may be chosen from a pyronine dye and a rhodamine Dye.

The pyronine dye may be chosen from pyronine Y and pyronine B.

The rhodamine dye may be chosen from rhodamine B, rhodamine G and rhodamine WT.

The fluorone dye may be chosen from fluorescein and fluorescein derivatives.

The fluorescein derivative may be chosen from phloxine B, rose bengal, and merbromine.

The fluorescein derivative may be chosen from eosin Y, eosin B and erythrosine B.

The azo dye may be chosen from methyl violet, neutral red, para red, amaranth, carmoisine, allura red AC, tartrazine, orange G, ponceau 4R, methyl red, and murexide-ammonium purpurate.

The biological stain may be chosen from saffranin O, basic fuchsin, acid fuschin, 3,3' dihexylocarbocyanine iodide, carminic acid, and indocyanine green.

The carotenoid may be chosen from crocetin, α-crocin (8,8-diapo-8,8-carotenoic acid), zeaxanthine, lycopene, α-carotene, β-carotene, bixin, and fucoxanthine.

The carotenoid may be present in the composition as a mixture chosen from saffron red powder, annatto extract and brown algae extract.

The antibacterial periodontal composition may further comprise at least one chelating agent.

The chelating agent may be chosen from ethylenediaminetetraacetic acid (EDTA) and ethylene glycol tetraacetic acid (EGTA).

The following terms are defined below.

The term "hydrophilic gelling agent" is intended to mean a material that thickens and stabilizes liquid solutions, emulsions, and suspensions. Hydrophillic gelling agents dissolve in liquid and provide a structure giving the resulting gel an appearance of a solid matter, while being mostly composed of a liquid. Hydrophillic gelling agents are very similar to thickeners.

The term "actinic light" is intended to mean light energy emitted from a specific light source (lamp, LED, or laser) and capable of being absorbed by matter (e.g. the photoactivator defined below) and produce an identifiable or measurable change when it interacts with it; as clinically identifiable change we can presume a change in the color of the photoactivator used (e.g. from red to transparent).

The term "photoactivator" is intended to mean a chemical compound capable of absorbing actinic light. The photoactivator readily undergoes photoexcitation and then transfers its energy to other molecules, thus enhancing or accelerating the dispersion of light, and enhancing or activating the oxidant present in the reaction mixture.

The term "oxidant" is intended to mean a either a chemical compound that readily transfers oxygen atoms and oxidize other compounds, or a substance that gains electrons in a redox chemical reaction.

The term "chelating agent" is intended to mean a chemical that removes metal ions, such as iron, and holds them in solution.

The term "healing factor" is intended to mean a compound that promotes or enhances the healing or regenerative process of a tissue.

The term "time of exposure to actinic light" is intended to mean the time a tissue, skin or wound is exposed to actinic light per application of actinic light.

The term "total time of exposure to actinic light" is intended to mean the cumulative time a tissue, skin or wound is exposed to actinic light after several application of actinic light.

The term "pharmacologically acceptable carrier" is intended to mean a preservative solution, a saline solution, an isotonic (about 0.9%) saline solution, or about a 5% albumin solution, suspension, sterile water, phosphate buffered saline, and the like. Other buffering agents, dispersing agents, and inert non-toxic substances suitable for delivery to a patient may be included in the compositions of the present invention. The compositions may be solutions, suspensions or any appropriate formulation suitable for administration, and are typically sterile and free of undesirable particulate matter. The compositions may be sterilized by conventional sterilization techniques.

The term "active oxygen species" is intended to mean chemically-reactive molecules containing oxygen. Examples include oxygen ions and peroxides. They can be either inorganic or organic. Active oxygen species are highly reactive due to the presence of unpaired valence shell electrons. They are also referred to as "reactive oxygen", "active oxygen, or "reactive oxygen species".

The term "mouth" is intended to mean the entire oral cavity, which includes the lips, gingiva (gums), the hard and soft palate, the uvula, palatine tonsils, the teeth, the inside of the cheeks, the tongue and the papillae of the tongue.

The term "periodontal pocket" is intended to mean the presence of an abnormally deepened gingival sulcus as it contacts a tooth. The gingival sulcus (groove) is the potential space between a tooth and the surrounding gingival tissue and is lined by sulcular epithelium. The depth of the sulcus is bounded by two entities: apically by the gingival fibers of the connective tissue attachment and coronally by the free gingival margin. When the sulcular depth is in excess of three millimeters on a constant basis, even regular toothbrushing will be unable to properly cleanse the depths of the sulcus, allowing food debris and microbes to accumulate and pose a danger to the periodontal ligament fibers attaching the gingiva to the tooth. If allowed to remain for too long of a period of time, these microbes, together with the enzymatic particles they produce, will be able to penetrate and ultimately destroy the delicate soft tissue and periodontal attachment fibers, leading to an even further deepening of the sulcus (beyond three millimiters), resulting in a periodontal pocket.

Features and advantages of the subject matter hereof will become more apparent in fight of the following detailed description of selected embodiments, as illustrated in the accompanying figures. As will be realized, the subject matter disclosed and claimed is capable of modifications in various respects, ail without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

In accordance with one embodiment, there is provided a use of a photoactivated composition for the manufacture of a medicament for oral disinfection and/or the treatment of an oral disease, m which the composition comprises:
  at least one oxidant,
  at least one photoactivator capable of activating the oxidant; and
  at least one healing factor chosen from hyaluronic acid, glucosamine and allantoin,
  in association with a pharmacologically acceptable carrier.

In accordance with another embodiment, there is provided a use of a photoactivated composition for oral disinfection, in which the composition comprises:
  at least one oxidant;
  at least one photoactivator capable of activating the oxidant; and
  at least one healing factor chosen from hyaluronic acid, glucosamine and allantoin;
  in association with a pharmacologically acceptable carrier.

In accordance with another embodiment, there is provided a use of a photoactivated composition for the treatment of an oral disease, in which the composition comprises:
  at least one oxidant;
  at least one photoactivator capable of activating the oxidant; and
  at least one healing factor chosen from hyaluronic acid, glucosamine and allantoin;
  in association with a pharmacologically acceptable earner.

In accordance with yet another embodiment, there is provided a use of a photoactivated composition for the treatment of periodontitis, wherein said composition comprises:
  at least one oxidant;
  at least one photoactivator capable of activating the oxidant; and
  at least one healing factor chosen from hyaluronic acid, glucosamine and allantoin;

in association with a pharmacologically acceptable carrier.

In accordance with another embodiment, there is provided method of full mouth disinfection and photodynamic assisted oral treatment of a patient which comprises the steps of:
  a) applying in a patients mouth a composition comprising at least one oxidant, at least one photoactivator capable of activating the oxidant: and at least one healing factor chosen from hyaluronic acid, glucosamine and allantoin; and
  b) treating said mouth of step a) to actinic light for a time sufficient for said photoactivator to cause activation of said oxidant.

Periodontal diseases caused by bacterial infection may also be treated with the composition of the present invention. Oral diseases, such as gingivitis, periodontitis, periodontal disease, oral thrush, lichen planus, and stomatitis may also be treated with the composition.

The composition comprises a number of active principles selected from groups of possible components. These various active principles each have their mechanism of action.

Oxidants

The composition comprises oxidants as a source of oxygen radicals. Peroxide compounds are oxidants that contain the peroxy group (R—O—O—R), which is a chainlike structure containing two oxygen atoms, each of which is bonded to the other and a radical or some element. Suitable oxidants for preparation of the active medium include, but are not limited to:

Hydrogen peroxide ($H_2O_2$) is the starting material to prepare organic peroxides, $H_2O_2$ is a powerful oxidizing agent, and the unique property of hydrogen peroxide is that it breaks down into water and oxygen and does not form any persistent, toxic residual compound. Hydrogen peroxide for use in this composition can be used in a gel, for example with 6% hydrogen peroxide. A suitable range of concentration over which hydrogen peroxide can be used in the present composition is less than about 12%, or from about 1% to about 12%, preferably from about 3.5% to about 12% and most preferably from about 3.5% to about 6%.

Urea hydrogen peroxide (also known as urea peroxide, carbamide peroxide or percarbamide) is soluble in water and contains approximately 36% hydrogen peroxide. Carbamide peroxide for use in this composition can be used as a gel, for example with 16% carbamide peroxide that represents 5.6% hydrogen peroxide. A suitable range of concentration over which urea peroxide can be used in the present composition is less than 36%, or from about 3% to about 38%, and preferably from about 10% to about 38% and most preferably from about 3% to about 16%. Urea peroxide brakes down to urea and hydrogen peroxide in a slow-release fashion that can be accelerated with heat or photochemical reactions. The released urea [carbamide, $(NH_2)CO_2)$], is highly soluble in water and is a powerful protein denaturant. It increases solubility of some proteins and enhances rehydration of the skin and/or mucosa.

Benzoyl peroxide consists of two benzoyl groups (benzoic acid with the H of the carboxylic acid removed) joined by a peroxide group. It is found in treatments for acne, in concentrations varying from 2.5% to 10%. The released peroxide groups are effective at killing bacteria. Benzoyl peroxide also promotes skin turnover and clearing of pores, which further contributes to decreasing bacterial counts and reduce acne. Benzoyl peroxide breaks down to benzoic acid and oxygen upon contact with skin, neither of which are toxic. A suitable range of concentration over which benzoyl peroxide can be used in the present composition is less than about 10%, or from about 1% to about 10%, or preferably from about 1% to about 8%, and most preferably from about 2.5% to about 5%.

Suitable oxydants may also include peroxy acids and alkali metal percarbonates, but the inclusion of any other forms of peroxides (e.g. organic or inorganic peroxides) should be avoided due to their increased toxicity and their unpredictable reaction with the pbotodynamic energy transfer.

Photoactivators

The photoactivators transfer light energy to the oxidants. Suitable photoactivators can be fluorescent dyes (or stains), although other dye groups or dyes (biological and histological dyes, food colorings, carotenoids) can also be used. Combining photoactivators may increase photo-absorbtion by the combined dye molecules and enhance absorption and photo-biomodulation selectivity. This creates multiple possibilities of generating new photosensitive, and/or selective photoactivator mixtures.

An advantageous characteristic of a photoactivator is increased Fluorescence. In the present invention, re-emission of light in the green to yellow spectrum would be advantageous, since it is a deep penetrating wavelength range, with deep absorption by the blood. This confers a strong increase on the blood flow, vasodilatation and angiokinetic phenomena. Suitable photoactivators include, but are not limited to:

Xanthene Derivatives

The xanthene derivative dyes have been used and tested for a long time worldwide. They display low toxicity and increased fluorescence. The xanthene group consists of 3 sub-groups that are: a) the fluorenes: b) fluorones; and c) the rhodoles.

The fluorenes group comprises the pyronines (e.g. pyronine Y and B) and the rhodamines (e.g. rhodamine B, G and WT). Depending on the concentration used, both pyronines and rhodamines may be toxic and their interaction with light may lead to increased toxicity. Similar effects are known to occur for the rhodole dye group.

The fluorone group comprises the fluorescein dye and the fluorescein derivatives.

Fluorescein is a fluorophore commonly used in microscopy with an absorption max. of 494 nm and an emission max. of 521 nm. The disodium salt of fluorescein is known as D&C Yellow 8. It has very high fluorescence but photodegrades quickly, in the present composition, mixtures of fluorescein with other photoactivators such as indocyanin green and/or saffron red powder will confer increased pbotoabsorption to these other compounds.

Eosins group comprises Eosin Y (tetrabromofluorescein, acid red 87, D&C Red 22) with an abs. max 514-518 nm, stains cytoplasm of cells, collagen, muscle fibers and red blood cells intensely red; and Eosin B (acid red 91, eosin scarlet, dibromo-dinitrofluorescein), with the same staining characteristics as Eosin Y. Eosin Y and eosin B are collectively referred to as "Eosin", and use of the term "Eosin" refers to either Eosin Y, Eosin B or a mixture of both. Eosin Y, eosin B, or a mixture of both can be used because of their sensitivity to the light spectra used: broad spectrum blue light, blue to green light and green light. Their tissue and biofilm staining properties and their low toxicity are also advantageous. Both eosin Y and eosin B stain red blood cells and thus confer to the composition of the present invention haemostatic (controls the flow or stops the flow of blood) properties as well as increase the selective targeting of light to the soft tissues of the lesion or wound during the application of the composition. In embodiments, the composition includes in the range of less than about 12% of at least one of Eosin B or Eosin Y or combinations thereof, or from about 0.02% to about 12% of at least one of Eosin B or Eosin Y or combinations thereof, or between about 0.02% and about 1.2%, or from about 0.02% to about 0.5%, or from about 0.5% to about 0.8% of at least one of Eosin 8 or Eosin Y or combinations thereof. In yet another embodiment, the composition includes less than 12% of at least one of Eosin B or Eosin Y or combinations thereof, or from about 0.02% to about 12% of at least one of Eosin B or Eosin Y or combinations thereof, or between about 0.02% and about 1.2%, or from about 0.02% to about 0.5%, or from about 0.02% to about less than 0.5% or from about 0.5% to about 0.8% of at least one of Eosin B or Eosin Y or combinations thereof, and/or less than about 2% Erythrosma B, or from about 0.005 to about 2% Erythrosine B, or from about 0.005% to about 1%, or about 0.01% to about 1%, or about 0.005% and about 0.15% of Erythrosine B.

Phloxine B (2,4,5,7 tetrabromo 4,5,8,7,tetrachlorofluorescein, D&C Red 28, acid red 92) is a red dye derivative of fluorescein which is used for disinfection and detoxification of waste water through photooxidation. It has an abs. max. of 535-548 nm. It is also used as an intermediate for making photosensitive dyes and Drugs.

Erythrosine B, or simply Erythrosine (acid red 61, tetraiodofluorescein) is a cherry-pink, coal-based fluorine food dye used as a biological stain, and a biofilm and dental plaque disclosing agent, with max. abs. 524-530 nm in aqueous solution. It is subject to photodegradation. Erythrosine is also used in some embodiments due to its photosensitivity to the light spectra used and its ability to stain biofilms. Inclusion of erythrosine should be favored when using the composition in deep pockets of infected or contaminated tissue, such as periodontal pockets in periodontal therapy. In embodiments, the composition includes in the range of less than about 2% Erythrosine B, or from about 0.005 to about 2% Erythrosine B, or from about 0.005% to about 1%, or about 0.01% to about 1%, or about 0.005% and about 0.15% of Erythrosine B.

Rose Bengal (4,5,6,7 tetrachloro 2,4,5,7 tetraiodofluorescein, acid red 94) is a bright bluish-pink biological dye with an absorption max. of 544-549 nm, that has been used as a dye, biological stain and diagnostic aid. Also used in synthetic chemistry to generate singlet from triplet oxygen.

Merbromine (mercurochrome) is an organo-mercuric disodium salt of fluorescein with an abs. max. of 508 nm. It is used as an antiseptic.

Azo Dyes

The azo (or diazo-) dyes share the N—N group, called azo the group. They are used mainly in analytical chemistry or as food colorings and are not fluorescent. Suitable azo dyes include: Methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), murexide-ammonium purpurate.

Biological Stains

Dye molecules commonly used in staining protocols for biological materials can also be used as photoactivators. Suitable biological stains include:

Saffranin (Saffranin 0, basic red 2) is also an azo-dye and is used in histology and cytology. It is a classic counter stain in a Gram stain protocol.

Fuchsin (basic or acid) (rosaniline hydrochloride) is a magenta biological dye that can stain bacteria and has been used as an antiseptic. It has an abs. max. 540-555 nm.

3,3' dihexylocarbocyanine iodide (DIOC6) is a fluorescent dye used for staining cell's endoplasmic reticulum, vesicle membranes and mitochondria. It shows photodynamic toxicity; when exposed to blue light, has a green fluorescence.

Carminic acid (acid red 4, natural red 4) is a red glucosidal hydroxyanthrapurin naturally obtained from cochineal insects.

Indocyanin green (ICG) is used as a diagnostic aid for blood volume determination, cardiac output, or hepatic function. ICG binds strongly to red blood cells and when used in mixture with fluorescein, it increases the absorption of blue to green light.

Carotenoids

Carotenoid dyes can also act as photoactivators.

Saffron red powder is a natural carotenoid-containing compound. Saffron is a spice derived from crocus sativus. It is characterized by a bitter taste and iodoform or hay-like fragrance; these are caused by the compounds picrocrocin and saffranal. It also contains the carotenoid dye crocin that gives its characteristic yellow-red color.

Saffron contains more than 150 different compounds many of them are carotenoids; mangicrocin, reaxanthine, lycopene, and various $\alpha$ and $\beta$-carotenes, that show good absorption of light and beneficial biological activity. Also saffron can act as both a photon-transfer agent and a healing factor. Saffron color is primarily the result of a-crocin (8,8 diapo-8,8-carotenoid acid). Dry saffron red powder is highly sensitive to fluctuating pH levels and rapidly breaks down chemically in the presence of light and oxidizing agents. It is more resistant to heat. Data show that saffron has anticarcinogenic, immunomodulating and antioxidant properties. For absorbance, it is determined for the crocin specific photon wavelength of 440 nm (blue light). It has a deep red colour and forms crystals with a melting point of 186° C. When dissolved in wafer if forms an orange solution.

Crocetin is another compound of saffron that was found to express an antilipidemic action and promote oxygen penetration in different tissues. More specifically it was observed an increased oxygenation of the endothelial cells of the capillaries. An increase of the oxygenation of muscles and cerebral cortex was observed and led to an increased survival rate in laboratory animals with induced hemorrhagic shock or emphysema.

Anatto a spice contains as main constituent (70-80%) the carotenoid bixin which displayed relevant antioxidative properties.

$\beta$-carotene, also displayed suitable characteristics.

Fucoxanthine is a constituent of brown algae with a pronounced ability for photosensitization of red-ox reactions.

Healing Factors

Healing factors comprise compounds that promote or enhance the healing or regenerative process of the tissues on the application site of the composition. During the photoactivation of the composition, there is an increase of the absorption of molecules at the treatment site by the mucosa. An augmentation in the blood flow at the site of treatment is observed for an extent period of time. An increase in the lymphatic drainage and a possible change in the osmotic equilibrium due to the dynamic interaction of the free radical cascades can be enhanced or even fortified with the inclusion of healing factors. Suitable healing factors include, but are not limited to:

Hyaluronic acid (Hyaluronan, hyaluronate): is a non-sulfated glycosaminoglycan, distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissues hydrodynamics, movement and proliferation of cells and participates in a wide number of cell surface receptor interactions, notably those including primary receptor CD44. The hyaluronidases enzymes degrade hyaluronan. There are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. In addition, recent studies show that hyaluronan fragments, but not the native high molecular mass of hyaluronan, can induce inflammatory responses in macrophages and dendritic cells in tissue injury. Hyaluronic acid is well suited to biological applications targeting the skin. Due to its high biocompatibility, it is used to stimulate tissue regeneration. Current studies evidenced hyaluronic acid appearing in the early stages of healing to physically create room for white blood cells that mediate the immune response. It is used in the synthesis of biological scaffolds for wound healing applications and in wrinkle treatment. In embodiment, the composition includes in the range of less than about 2% hyaluconic acid, or from about 0.001% to about 2%, or preferable from about 0.002% to about 2%, or from about 0.002% to about 1% hyaluronic acid.

Glucosamine: is one of the most abundant monosaccharides in human tissues and a precursor in the biological synthesis of glycosilated proteins and lipids. It is commonly used in the treatment of osteoarthritis. The common form of glucosamine used is its sulfate salt. Glucosamine shows a number of effects including an anti-inflammatory activity, stimulation of the synthesis of proteoglycans and the synthesis of proteolytic enzymes. A suitable range of concentration over which glucosamine can be used in the present composition is from less than about 5%, or from about 0.0001% to about 5%, or from about 0.0001% to about 3%, and preferable from about 0.001% to about 3%, or from about 0.011% to about 1% and about about 1% to about 3%.

Allantoin: is a diureide of glyosilic acid. It has keratolytic effect, increases the wafer content of the extracellular matrix, enhances the desquamation of the upper layers of dead (apoptotic) skin cells, and promotes skin proliferation and wound healing. In embodiment, the composition includes in the range of less than about 1% allantoin, or from about 0.001% to about 1%, or from about 0.002% to about 1%, or preferably from about 0.02% to about 1%, and most preferably from about 0.02% to about 0.5%.

Also, saffron can act as both a photon-transfer agent and a healing factor.

Chelating Agents

Chelating agents can be included to promote smear layer removal in closed infected pockets and difficult to reach lesions; act as a metal ion quencher and as a buffer. Suitable chelating agents include, but are not limited to:

Ethylenediaminotetraacetic acid (EDTA): It is an amino acid, used to sequester di- and trivalent metal ions. EDT A binds to metals via 4 carboxylate and 2 amine groups. EDTA forms especially strong complexes with Mn(III), Fe(III), Cu(III), Co(III). Prevents collection of the platelets and blood clots formation. It is used in the endodontic therapy as a smear layer removal agent during instrumentation. It is used to buffer solutions.

Ethylene glycol tetraacatic acid (EGTA): is related to EDT A, but with a much higher affinity for calcium than for magnesium ions. It is useful for making buffer solutions that resemble the environment inside living cells and is often employed in dentistry, more specifically endodontics, in the removal of smear layer.

Hydrophilic Gelling Agents

The antibacterial periodontal composition may also contain one or more hydrophilic gelling agent. The hydrophilic gelling agent enhances the consistency of the composition and contributes to facilitating the application of the composition to the skin or wounded area. Also, when used with hydrogen peroxide ($H_2O_2$), it may contribute to the slow the release of the $H_2O_2$, and provide a more immediate reaction because pure $H_2O_2$ can be used directly. Suitable hydrophilic gelling agent include, but are not limited to glucose, modified starch, methyl cellulose, carboxymethyl cellulose, propyl cellulose, hydroxypropyl cellulose, Carbopol® polymers, alginic acid, sodium alginate, potassium alginate, ammonium alginate, calcium alginate, agar, carrageenan, locust bean gum, pectin, and gelatin.

Photoactivation

The inclusion of suitable photosensitive compounds and activation with a light source of a proper wavelength, leads to the acceleration in the breakdown process of the source of peroxide (the oxidant) and the other reactions that take place, via a photodynamic phenomenon. The included photosensitive compounds are illuminated by photons of a certain wavelength and excited to a higher energy state. When the photoactivators' excited electrons return to a lower energy state, they emit photons with a lower energy level, thus causing the emission of light of a longer wavelength (Stokes shift). In the proper environment much of this energy transfer is transferred to oxygen or the reactive hydrogen peroxide and causes the formation of active oxygen species, such as singlet oxygen and other active oxygen.

The singlet oxygen and other active oxygen species generated by the activation of the composition are thought to operate in a hermetic fashion. That is, a health beneficial effect is brought about by the low exposure to a normally toxic stimuli (e.g. active oxygen), by stimulating and modulating stress response pathways in cells of the targeted tissues. Endogenous response to exogenous generated free radicals (active oxygen species) is modulated in increased defense capacity against the exogenous free radicals and induces acceleration of healing and regenerative processes. Furthermore, primary activation of the composition will also produce a secondary antibacterial effect. The extreme sensitivity of bacteria to exposure to free radicals makes the composition of the present invention a de facto bactericidal composition.

Possible mechanism of action should be a fortified redox signalling phenomenon resulting in accentuated signal transduction process in which cells convert one kind of signal into another; activated "second messengers" induce a "signal cascade" beginning with a relatively small stimulus that elicits a large response via biologically monitored amplification of such signals. These complex mechanisms act possibly involving angiogenic phenomena via growth factor activation.

This method could be described as a form of photodynamic therapy. However, unlike other photodynamic techniques, where the photoactoactivators are incorporated in the tissue structure, in the present method, the photoactive material is in simple contact with the tissue and acts when activated by light, as a "photodynamic device". Additionally, the actinic light penetrates the tissue, and the light that is emitted by the photoactivator (light of a longer wavelength) is absorbed by the tissue.

Any source of actinic light can be used. Any type of halogen, LED or plasma arc lamp, or laser may be suitable. The primary characteristic or suitable sources of actinic light will be that they emit light in a wavelength (or wavelengths) appropriate for activating the one or more photoactivators present in the composition. In one embodiment, an argon laser is used. In another embodiment, a potassium-titanyl phosphate (KTP) laser (e.g. a Greenlight™ laser) is used. In yet another embodiment, a LED photocuring device is the source of the actinic light. In yet another embodiment the source of the actinic light is a source of visible light having a wavelength between 400 and 700 nm, and preferably from 400 and 600 nm and most preferably from 450 to 700 nm. Furthermore, the source of actinic light should have a suitable power density. Suitable power density for non-collimated light sources (LED, halogen or plasma lamps) are in the range from about 800 $mW/cm^2$ to about 3000 $mW/cm^2$, and preferably from about 900 $mW/cm^2$ to about 2000 $mW/cm^2$. Suitable power density for laser light sources are in the range from about 0.5 $mW/cm^2$ to about 0.8 $mW/cm^2$.

The duration of the exposure to actinic light will be dependent on the surface of the treated area, and on the type of lesion, trauma or injury that is being treated. The photo-activation of the composition may take place within seconds or even fragment of seconds, but a prolonged exposure period is beneficial to exploit the synergistic effects of the absorbed, reflected and reemitted light on the composition of the present invention and its penetration in the tissue being treated. In one embodiment, the time of exposure to actinic light of the tissue on which the antibacterial periodontal composition has been applied is a period of less than 5 minutes. In another embodiment, the time of exposure is from about 20 seconds to about 5 minutes, or from between about 60 second and about 5 minutes. In another embodiment, the time of exposure to actinic light of the tissue on which the antibacterial periodontal composition has been applied is a period of less than about 5 minutes. In another embodiment the time of exposure is between about 20 seconds to about 5 minutes, or between about 60 seconds and about 5 minutes per $cm^2$ of the area to be treated, so that the total time of exposure of a 10 $cm^2$ area would be between 10 minutes and 50 minutes. In yet another embodiment, the source of actinic light is in continuous motion over the treated area for the appropriate time of exposure. In yet another embodiment, multiple applications of the antibacterial periodontal composition and actinic light are performed. In some embodiments, the tissue, skin or wound is exposed to actinic light at least two, three, four, five or six times, or more, depending on the patient's requirement. Also, the entire treatment may be repeated in its entirety as may be required by the patient. In some embodiments, a fresh application of the antibacterial periodontal composition is applied before exposure to actinic light.

Oral Diseases

The present invention may be used to treat, or at least participate in the treatment of various oral diseases. Such oral diseases include but are not limited to:

Gingivitis

Gingivitis is a disorder that is defined by the inflammation of the gums, and is characterized as a periodontal disease, which are characterized by the destruction of the gums, tissue, tooth sockets, and ligaments which create the structure that holds the teeth in place. Gingivitis is one of the first stages of serious periodontal disease.

The symptoms of gingivitis include swollen gums, mouth sores, a bright red or purple appearance to the gums, shiny gums, gums that are painless except when touched, and bleeding gums. Often the first signs of gingivitis have no symptoms except for visual symptoms and is likely only to be diagnosed by a dental professional.

Periodontal Disease

Periodontal disease is also known as trench mouth. Periodontal disease leads to severe gingivitis and can cause gums to bleed, ooze pus, is highly painful, and often leads to premature tooth loss. While most developed nations have fewer cases of periodontal disease, it does still exist simply due to the high number of employed, working class Americans who are not given dental insurance as part of their benefits package. Dental work is very expensive, and not all patients can afford good dental care.

Periodontal disease is more prevalent in developing nations and in most cases, a professional cleaning and antibiotics can clear up most cases of periodontal disease. However, if left untreated the infection can spread throughout the body and can lead to serious health complications.

Symptoms of periodontal disease include painful gums, bad breath, a foul taste to the mouth, fever, gums that bleed with only mild amounts of pressure, crater sized canker sores between the teeth and gums, swollen lymph nodes around the head, neck, or jaw, a gray film on the gums, red gums, swollen gums, and pain when eating and swallowing.

Periodontitis

Periodontitis or *Pyorrhea alveolaris* is the inflammation of the periodontium which comprises tissues supporting the teeth in the oral cavity. Parts included in the periodontium are the gingiva (gum tissue), the alveolar bone which are sockets where teeth are attached, the cementum or outer layer of teeth roots and the periodontal ligaments or PDL composed of connective tissue fibers linking the gingival and cementum to the alveolar bone. The condition is described as the progressive loss of bone around teeth leading to loose teeth or loss of teeth if left unattended.

There are different causes for the disease in which bacteria is the most common. Periodontitis is considered as an advanced phase of gum disease since it already involves bone loss in the area. It is the effect of mild gingivitis being left untreated. Due to the presence of bacterial infection, the body can also respond negatively to it leading to further complications. The condition is one of the leading causes of tooth loss among adults, affecting around 50% of everyone over the age of 30.

Signs and symptoms arise due to the unstable anchoring of teeth as well as the presence of microorganisms. Gums occasionally or frequently bleed or turn red while brushing teeth, using dental floss, biting into food, chewing or touching with fingers. Gums swell or develop pus occasionally as well. The affected individual likely have halitosis or bad breath and have a lingering metallic or tinny taste inside the mouth. Teeth seem longer and sharper due to gingival recession which partly may also be caused by hard brushing. If enzymes called collagenases have begun destroying collagen, the person will have deep pockets between the teeth and gums.

During the early stages of periodontal disease, only a few signs and symptoms may be noticeable. Aggressive periodontitis may affect younger individuals and can occur in episodes. Some episodes may present very mild symptoms while others may be very severe. The signs and symptoms especially in the case of chronic periodontitis are usually progressive in nature.

Oral Thrush

Oral thrush is the condition where the fungus *Candida albicans* grows rapidly and uncontrollably in the mouth. The bacterium known as flora keeps the growth of *Candida albicans* under control in a healthy body. Oral thrush presents with creamy white paste that covers the tongue, and can spread rapidly to the roof of the mouth, gums, back of the throat, tonsils, and the inside of the cheeks. Babies, toddlers, older adults, and patients whose immune systems have been somehow compromised are most likely to come down with oral thrush.

Symptoms of oral thrush begin with a white pasty covering over the tongue and inside of the cheeks. As the oral thrush continues to develop, it can cause a mild amount of bleeding if the tongue is scraped or when the patient brushes their teeth. These symptoms may develop very quickly, but thrush can last for months. If the lesions of oral thrush spread down the esophagus, the patient may develop addition symptoms such as difficulty swallowing, the sensation of food being caught in the throat or the middle of the chest, and a fever should the Infection continue to spread past the esophagus.

Lichen Planus

Lichen planus is most often defined as an oral disease that affects the lining of the mouth with inflammation. Lichen planus is most often recognized as a rash that irritates the tissue of the oral cavity. Most patients come down with their first case between the age of 45 and 80, although a slowly increasing number of reports dealing with younger patients have trickled in. While lichen planus is most often associated with the interior of the cheeks, many cases will find the entire mouth is affected, including the gums, the tongue, the lips, and in rare cases, the throat or esophagus. Lichen planus also occurs on the skin, as a skin disease, and often must be referred to specifically as skin lichen planus to differentiate between the oral type.

Lichen planus is a self contained disease that can last for weeks, months, and in some cases, years. It is not contagious. It is often mistaken for genital diseases, as the genitalia are often the most noticeably affected during the early development stage. Because the symptoms and outbreaks occur rapidly and then disappear, often for weeks, treatment is difficult. While some patients find great relief in cool compresses or tub soaks and cool baths, most patients require medical treatment in order to relieve their symptoms.

Stomatitis

Stomatitis basically means inflammation of the mouth, but more specifically, stomatitis is the inflammation of the mucous lining of the mouth which may include the gums, tongue, cheeks, lips and the floor or roof of the mouth. There are different types of stomatitis and classification is based on how the disease was acquired by a person. The two types of stomatitis are contact stomatitis and aphthous stomatitis. Contact stomatitis is an inflammation of the oral mucosa caused by coming in contact with allergens or irritants. It is classified by its pattern of distribution, etiologlc factors, and clinical features. There some cases of contact stomatitis that are left undetected because of the lack of clinical signs. Anybody can have contact stomatitis regardless of race, age and sex. Although it has been observed that if is more common in the elders.

Aphthous stomatitis, also known as canker sore or aphthous ulcers, has an unknown etiology. Just like contact stomatitis, canker sore affects the oral mucosa. An aphthous ulcer is a type of oral ulcer, which presents as a painful open sore inside the mouth or upper throat (including the uvula) caused by a break in the mucous membrane. The condition is also known as Sutton's Disease, especially in the case of major, multiple, or recurring ulcers. The ulcers can be described as shallow, discrete, and painful and are usually visible on the mucous membranes that are unattached. This type of stomatitis, just like contact stomatitis, is self limited and do not usually cause complications. The normal size of ulcers may last for 1 to 2 weeks but larger ulcers may last for months.

Herpes Simplex Lesions

Herpes simplex is a viral disease caused by herpes simplex viruses; both herpes simplex virus 1 (HSV-1) and herpes simplex virus 2 (HSV-2) cause herpes simplex. Infection with the herpes virus is categorized into one of several distinct disorders based on the site of infection. Oral Herpes, the visible symptoms of which are colloquially called cold sores, and infects the face and mouth. Oral herpes is the most common form of herpes simplex viruses infection.

Other Oral Inflammatory Lesions

The present invention may be used to treat other types of oral inflammation, including but not limited to oral mucositis, oral ulcers caused by viral, bacterial, fungal or protozoan infections, or caused by disorders of the immune system (immunodeficiency, autoimmunity, or allergy). Also included is Oral Submucous Fibrosis, a chronic debilitating disease of the oral cavity characterized by inflammation and progressive fibrosis of the submucosal tissues. Also included is Glossitis, an inflammation or infection of the tongue. It causes the tongue to swell and change color.

EXAMPLE I

An exemplary antibacterial periodontal composition is prepared by mixing the following components:

TABLE 1 exemplary antibacterial composition

| Oxidant | Photoactivators | Healing factor(s) |
| --- | --- | --- |
| Carbamide peroxide (16%) | Erythrosine B (0.5%) Eosin Y (0.25%) Saffron Red powder (0.25%) | Glucosamine sulfate (3%) Hyaluronic acid (3%) |

The oxidant (4 mL) and healing factors (1.5 mL) were mixed and combined with the photoactivators (1 mL). The resulting composition was applied to the mouth of a patient, and activated with actinic light provided by a LED photocuring device (blue light). The composition was removed following treatment.

EXAMPLE II

An second exemplary antibacterial periodontal composition is prepared by mixing the following components:

TABLE 2 exemplary antibacterial composition

| Oxidant | Photoactivators | Healing factor(s) |
| --- | --- | --- |
| Carbamide peroxide (16%) | Fluorescein Indocyanin green Saffron Red powder (0.25%) | Glucosamine sulfate (3%) Hyaluronic acid (3%) |

The oxidant (4 mL) and healing factors (1.5 mL) were mixed and combined with the photoactivators (1 mL). The resulting composition was applied to the mouth of a patient, and activated with actinic light provided by a LED photocuring device (blue light). The composition is removed following treatment.

This second exemplary composition is using the fluorescein dye as a photoactivator to other dyes (indocyanine green and saffron red powder) present in the composition. The addition of a small amount of fluorescein to the indocyanine green and saffron red powder solution caused reemission of light at wavelengths that activated the other dye compounds and improved the treatment by increasing the established clinical absorption/reemission criteria.

Indocyanine green binds well to hemoglobin and helps the selective energy absorption by the tissues and also helps targeting these tissues with the generated free radical cascades. Also, this photoactivators mixture is able to render saffron red fluorescent, which again improves both the photodynamic and biostimulating phenomena.

EXAMPLE III

Photodynamic therapy (PDT) has been introduced as an adjunctive new approach of antibacterial treatment that might compliment the conventional treatment. PDT is based on the principle that a photoactivatabie substance, the photosensitizes, binds to the target cell and can be activated by light of a suitable wavelength. During this process, free radicals are formed (among them singlet oxygen), which then produce an effect that is toxic to the cell.

A gel has been used comprising photosensitizers of specific absorption to blue-green light (450-530) that at the same time are bacterial disclosers. The substrate following reaction with biofilm releases healing factors that intervene in the regeneration mechanism of the mouth tissues (e.g. gum, periodontal tissues and oral mucosa). This gel has been applied to all treatment stages as follows:

The first session included meticulous Oral hygiene instructions (OHI). Thereafter the gel was applied in supragingival scaling facilitating the detachment of calculus and stains, conferring light anaesthesia and controlling bleeding during this procedure.

In the second session the gel was applied during full mouth subgingival instrumentation. Local anaesthesia was selectively needed. SRP was performed until the operator feels that the root surfaces are adequately debrided and planed. Subsequently the session was completed using the gel as a phofosensitiser which was applied with a blunt needle to the instrumented sites starting from the apical end of the pocket and moving coronally to avoid entrapment of air bubbles. A 532 nm KTP at 0.7 W power was applied into the pockets.

This new protocol diminished the number of sessions usually required for the conventional periodontal treatment; minimized the need of local anaesthesia during SRP; the operation field was clear; patients showed a great compliance the clinical parameters were dramatically improved 2 weeks following SRP+PTD.

EXAMPLE IV

Selection of Patients

Three healthy individuals (mean age 48.6±4.2 years). 1 females and 2 males, 1 smoker formed the test group. The control group comprised 3 healthy individuals (mean age 42.2±3.4 years) 1 female, 2 males, 1 smoker. All individuals showed evidence of Chronic Periodontitis (ChP) and were included in this preliminary study (Table 1).

All subjects were selected from a private dental clinic limited to periodontics in Piraeus, Greece. All participants gave their consent to take part in the study.

Periodontal Examination

Chronic periodontitis was defined according to international Classification of Periodontal Diseases (Armitage 1999). A full-mouth clinical examination was performed by the same calibrated examiner in each patient at baseline and two time points before active treatment and two weeks following active periodontal treatment (Table 5), using a manual probe (UNC 15, Hu Friedy. Chicago. Ill. USA). The following parameters were recorded at six sites per tooth, clinical attachment loss (CAL in mm), bleeding on probing (BOP in percentage of sites) and plaque index (PI in percentage of sites).

EXAMPLE V

Urea Peroxide Gel

The gel comprising photosensitizes (eosin)—of specific absorption to blue-green light (450-530 nm) that at the same time are bacterial disclosers capable of revealing bacteria. The basis is urea peroxide ($CH_6N_2O_3$) that releases $O_2$ and free radicals upon breakdown as well as healing factors that intervene in the regeneration mechanism of the tissues.

TABLE 3 exemplary antibacterial composition

| Oxidant | Photoactivators | Healing factor(s) |
|---|---|---|
| Carbamide peroxide (12%) | Eosin Y (0.012%) Erythrosine B (0.002%) | Glucosamine sulfate (0.01%) Hyaluronic acid (0.02%) |

EXAMPLE VI

Initial Examination OHI Supragingival Debridement

All patients went through a hygiene phase with detailed case presentation, supragingival debridement, tooth polishing and repeated oral hygiene instructions. The gel was used as an aid to the supragingival debridement procedure in the test group only.

Scaling/Root Planning

Two weeks following initial examination the patients received full mouth Scaling/root planning as follows:

Test Group

The test group received full mouth Scaling/roof planning under local anaesthesia as needed at all sites exhibiting a PD≥4 mm. SRP was completed within approximately 60 minutes. The gel was used during the mechanical procedure. Freshly sharpened Gracey curettes (Hu-Friedy, Leimen, Germany) and a piezoelectric ultrasonic scaler (Satelec® Suprasson® P-Max Lux Merignac Cede—France) were used in combination until the root surface felt smooth and clean to an explorer tip (EXP 11/12, Hu-Friedy, Leimen, Germany).

Subsequently the session was completed using the gel as a photosensitiser which was applied using a device with a blunt needle to the instrumented sites, which includes the periodontal site, starting from the apical end of the pocket and moving coronally to avoid entrapment of air bubbles.

The free gingiva and the part of the root tooth that was related to the periodontal site was also covered with the composition. A 532 nm KTP (Quanta System S.p.A., Solbiate Olona (VA)—Italy) at 0.7 W power was applied into the pockets (Photodynamic therapy). The laser was set to an irradiation time of 10 seconds. Beginning with the upper jaw each successive tooth was irradiated for 10 seconds on the vestibular side and 10 seconds on the oral side.

Control Group

The control group received full mouth Scaling/root planning per jaw under local anaesthesia at all sites exhibiting a PD≥4 mm SRP was completed within 60 minutes. Freshly sharpened Gracey curettes (Hu-Friedy, Leimen, Germany) and a piezoelectric ultrasonic scaler (Satelec® Suprasson® P-Max Lux. Merignac Cedex—France) were used in combination until the root surface felt smooth and clean to an explorer tip (EXD 11/12, Hu-Friedy, Leimen, Germany).

Both groups showed a significant reduction from Initial examination to two weeks following active treatment in all clinical parameters. In the test group, the CAL decreased from 5.92±1.92 mm at the first visit to 4.38±1.69 mm two weeks post treatment (a difference of 1.64 mm). In the control group the CAL decreased from 5.74±1.73 mm to 4.94±1.92 mm (a difference of 0.8 mm). The difference of BOP percentages in the test group from baseline to two weeks post treatment was 62.42 and in the control group 52.54.

The test group showed a trend to have a greater reduction in CAL and BOP from Initial examination to two weeks following active treatment as compared to control group.

TABLE 5

Clinical parameters at baseline and following treatment

| | Test group | | | Control group | | |
|---|---|---|---|---|---|---|
| Sessions | 1 | 2 | 3 | 1 | 2 | 3 |
| CAL (mm) Mean ± SD (Min, max) | 5.92 ± 1.92 (4, 8) | 5.44 ± 1.62 (4, 7) | 4.38 ± 1.69 (3, 5) | 5.74 + 1.73 (4, 7) | 5.31 ± 1.94 (4, 6) | 4.94 + 1.92 (3, 5) |
| BOP (%) | 79.17 | 43.53 | 16.75 | 73.29 | 42.29 | 18.75 |
| PI (%) | 65.63 | 42.31 | 21.08 | 60.95 | 42.18 | 27.08 |
| Treatment | Initial Examination OHI + Supragingival scaling | Full mouth SRP + Photodynamic therapy | | Initial Examination OHI + Supragingival scaling | Full mouth SRP Within 48 hours | |
| Time between sessions | Baseline | 2 weeks following initial examination | 2 weeks following treatment | | 2 weeks following initial examination | 2 weeks following treatment |

EXAMPLE VII

Results

Patient Characteristics at Baseline

The baseline characteristics of the 6 participants who were treated non-surgically or with the adjunctive use of the gel and photodynamic treatment are displayed in Table 4. None of the demographic and periodontal variables seem to show difference between the two groups.

TABLE 4

Demographics and Periodontal variables of Chronic Periodontitis patients at baseline

| Variables | Test group | Control group |
|---|---|---|
| Age | 48.6 ± 4.2 | 42.2 ± 3.4 |
| Male | 2 | 2 |
| Female | 1 | 1 |
| Smoker | 1 | 1 |
| Mean Number of teeth | 26.6 | 26.3 |
| Mean Number of sites | 160 | 156 |
| Plaque (%) | 65.63 ± 8.1 | 60.95 ± 3.9 |
| Bleeding on probing (%) | 79.17 ± 11.5 | 73.29 ± 12.4 |

Numerical date (CAL) were summarized as means and categorical data (BOP and PI) were summarized as frequency distribution (Table 5).

EXAMPLE VIII

Urea Peroxide Gel

The gel comprising photosensitizers (eosin Y)—of specific absorption to blue-green light (450-530 nm) that at the same time are bacterial disclosers capable of revealing bacteria. The basis is urea peroxide ($CH_6N_2O_3$) that releases $O_2$ and free radicals upon breakdown as well as healing factors that intervene in the regeneration mechanism of the tissues.

TABLE 6 exemplary antibacterial composition

| Oxidant | Photoactivators | Healing factor(s) |
|---|---|---|
| Carbamide peroxide (12%) | Eosin Y (0.012%) | Glucosamine sulfate (0.01%) Hyaluronic acid (0.02%) |

EXAMPLE IX

Patient Characteristics at Baseline

The baseline characteristics of 10 participants who were treated non-surgically or with the adjunctive use of the gel and photodynamic treatment are displayed in Table 7. None of the demographic and periodontal variables seem to show difference between the two groups.

TABLE 7

Demographics and Periodontal variables of Chronic Periodontitis patients at baseline.

| Variables | Test group SRP + PDT | Control group SRP |
|---|---|---|
| Age | 49.3 ± 5.2 | 46.9 ± 4.3 |
| Male | 3 | 2 |
| Female | 2 | 3 |
| Smoker | 2 | 2 |
| Mean Number of teeth | 27.1 | 26.4 |
| Plaque (%) | 61.5 ± 3.1 | 59.7 ± 6.8 |
| Bleeding on probing (%) | 55.6 ± 8.1 | 60.2 ± 3.9 |

Each group of patient was treated according to the protocol described in example VI above. Numerical data (CAL) were summarized as means and categorical data (BOP and PI) were summarized as frequency distribution (Table 8).

Both groups showed a significant reduction from Initial examination to six weeks following active treatment in all clinical parameters (See FIG. 4). In the test group, the CAL decreased from 5.9 mm at the first visit to 4.3 mm six weeks post treatment (a difference of 1.6 mm). In the control group the CAL decreased from 5.7 mm to 4.5 mm (a difference of 1.2 mm). The difference of BOP percentages in the test group from baseline six weeks post treatment was 30.2% in the treatment group and 21.5% in the control group (a difference of 8.7%). The difference of periodontal pocket depth (PPD) in the test group from baseline to six weeks post treatment was 2.1 mm, while in the control group it was 1.3 mm (a difference of 8 mm).

Figure 1A:
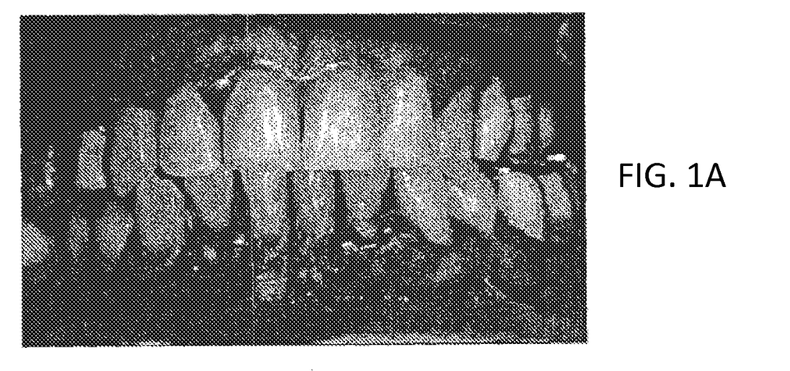
FIG. 1A is a picture illustrating a periodontitis in a patient to be treated with a method in accordance with an embodiment of the present invention.
Figure 1B:
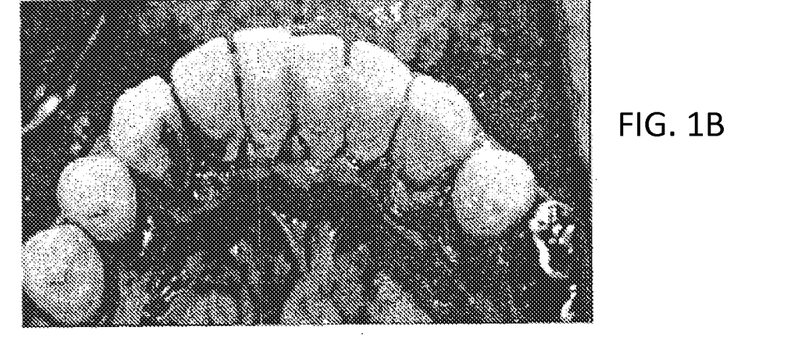
FIG. 1B is a picture illustrating a periodontitis in a patient to be treated with a method in accordance with an embodiment of the present invention.
Figure 1C:
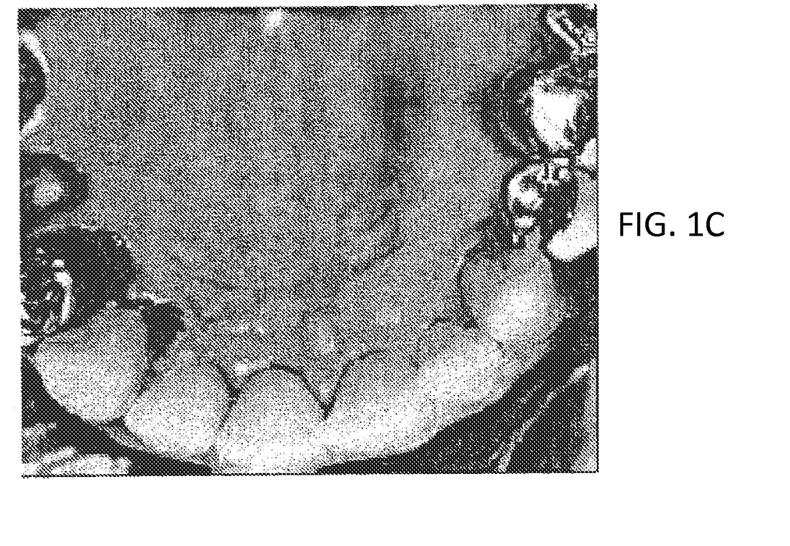
FIG. 1C is a picture illustrating a periodontitis in a patient to be treated with a method in accordance with an embodiment of the present invention.
Figure 2A:
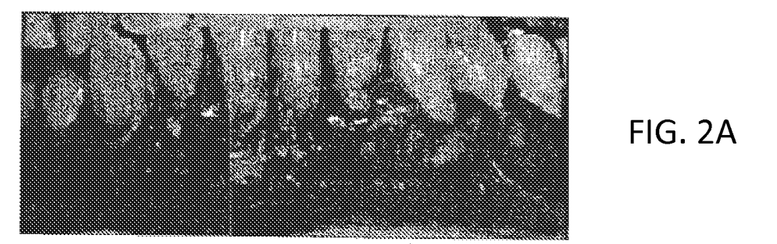
FIG. 2A is a picture illustrating a periodontitis in a patient to be treated with a method in accordance with an embodiment of the present invention.
Figure 2B:
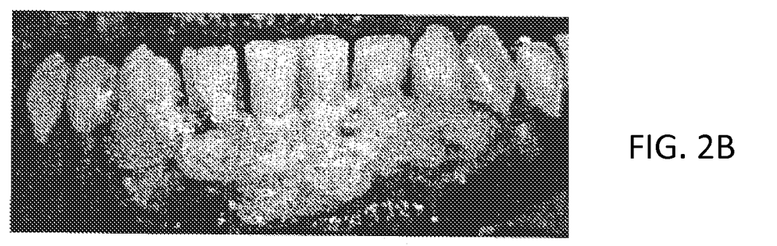
FIG. 2B is a picture illustrating a periodontitis in a patient being treated with a composition in accordance with an embodiment of the method of the present invention.
Figure 2C:
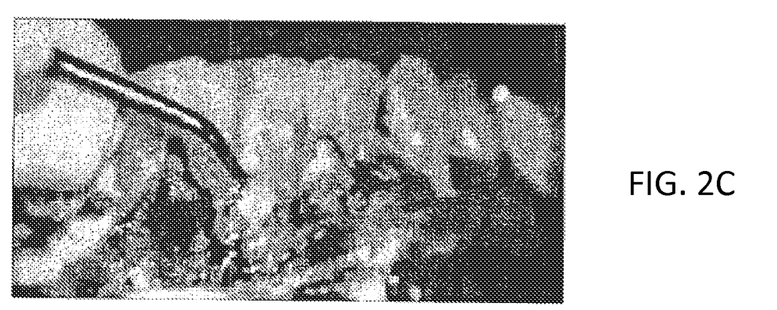
FIG. 2C is a picture illustrating a periodontitis in a patient being treated with a composition in accordance with an embodiment of the method of the present invention.
Figure 2D:
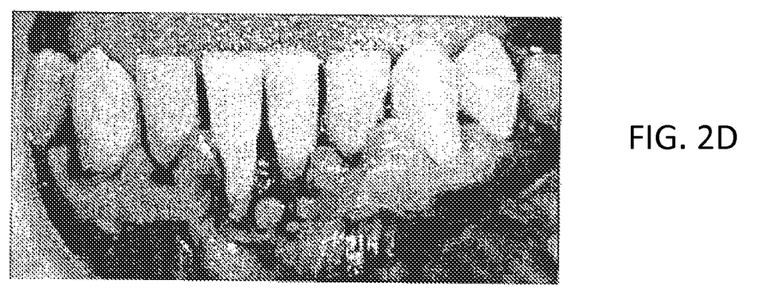
FIG. 2D is a picture illustrating a periodontitis in a patient having been treated with a composition in accordance with an embodiment of the method of the present invention.
Figure 3A:
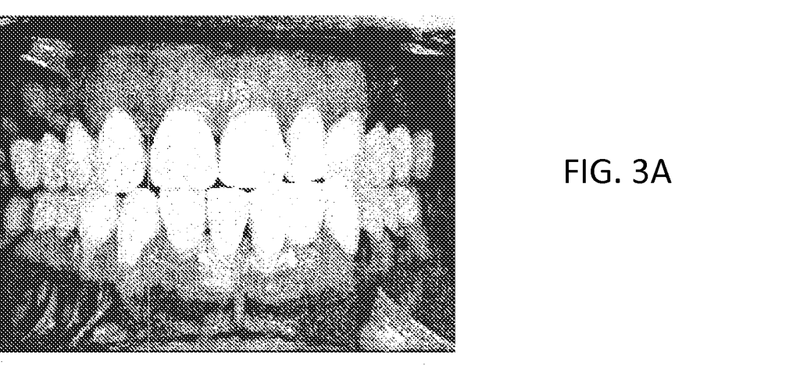
FIG. 3A is a picture illustrating a patient mouth and teeth two weeks after having been treated with a composition in accordance with an embodiment of the method of the present invention.
Figure 3B:
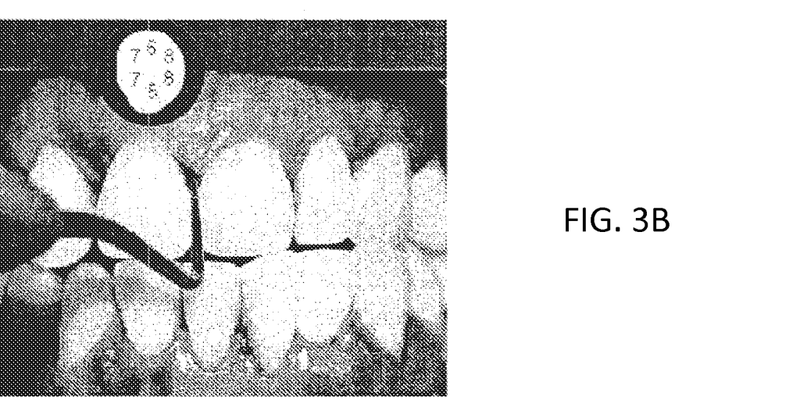
FIG. 3B is a picture illustrating the depth of a periodontal pocket in a patient mouth two weeks after having been treated with a composition in accordance with an embodiment of the method of the present invention.
Figure 3C:
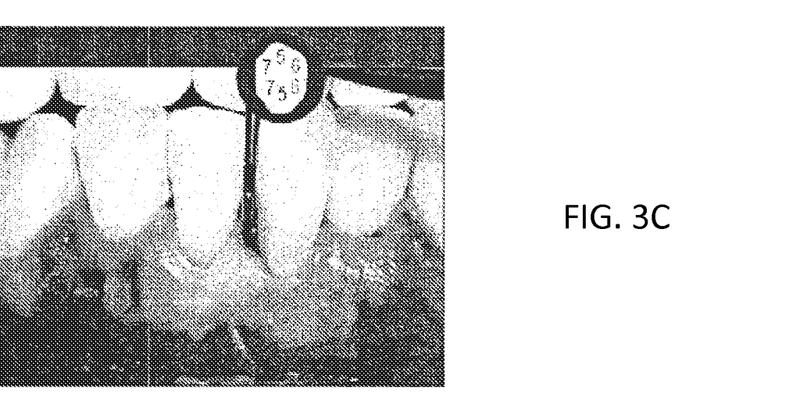
FIG. 3C is a picture illustrating the depth of a periodontal pocket in a patient mouth two weeks after having been treated with a composition in accordance with an embodiment of the method of the present invention.
Figure 4A:
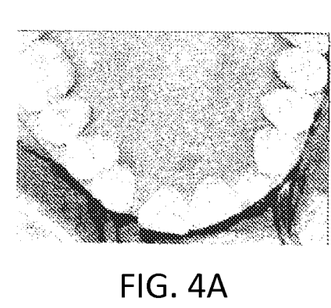
FIG. 4A is a picture illustrating a patient mouth and teeth six weeks after having been treated with a composition in accordance with an embodiment of the method of the present invention.
Figure 4B:
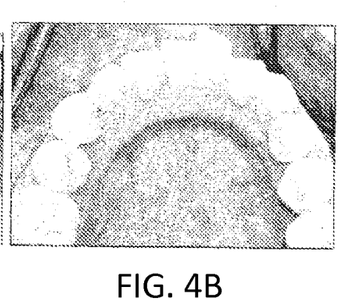
FIG. 4B is a picture illustrating a patient mouth and teeth six weeks after having been treated with a composition in accordance with an embodiment of the method of the present invention.
Figure 4C:
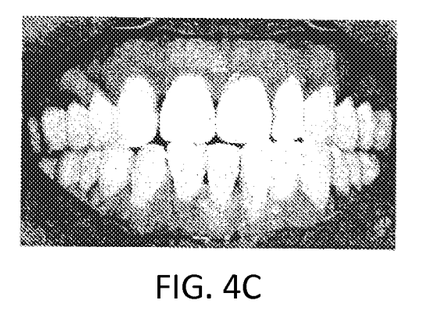
FIG. 4C is a picture illustrating a patient mouth and teeth six weeks after having been treated with a composition in accordance with an embodiment of the method of the present invention.
Figure 4D:
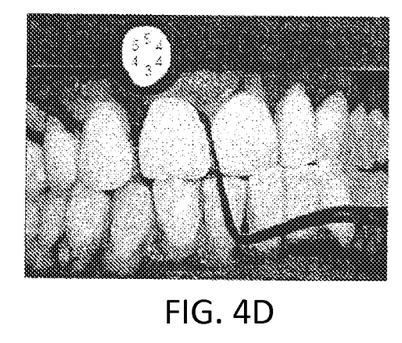
FIG. 4D is a picture illustrating the depth of a periodontal pocket in a patient mouth six weeks after having been treated with a composition in accordance with an embodiment of the method of the present invention.

The test group showed a trend to have a greater reduction in CAL and BOP from initial examination to two weeks following active treatment as compared to control group (See FIG. 3).

TABLE 8

Analysis of CAL, PPD and BOP between SRP and SRP + PDT at baseline and 6 weeks

| Variables | Control group SRP | Test group SRP + PDT |
|---|---|---|
| CAL (baseline) | 5.7 mm | 5.9 mm |
| CAL (6 weeks) | 4.5 mm | 4.3 mm |
| PPD (baseline) | 5.3 mm | 5.6 mm |
| PPD (6 weeks) | 4.0 mm | 3.5 mm |
| BOP (baseline) | 49.7% | 51.5% |
| BOP (6 weeks) | 28.2% | 21.3% |

TABLE 9

Mean differences between SRP and SRP + PDT at baseline and 6 weeks

| Variation (baseline − 6 weeks) | Control group SRP | Test group SRP + PDT |
|---|---|---|
| Δ CAL | 1.2 mm | 1.6 mm |
| Δ PPD | 1.3 mm | 2.1 mm |
| Δ BOP | 21.5% | 30.2% |

Furthermore, a visual analogue scale (VAS) is used to subjectively measure the pain and discomfort of the patient across a continuum of values, ranging from 0 (no pain) to 10 (unbearable), where values from about 1 to about 3 represent mild pain, values from about 3 to about 7 represent moderate pain, values from about 7 to about 9 represent severe pain, and values from about 8 to about 10 represent unbearable pain. The average VAS score for patients undergoing SRP is 2.32, while that of patient undergoing SRP with PDT had an average score of 0.52.

The protocol for periodontal treatment described in Example VI was applied in patients with chronic periodontitis. Over the course of the 6 weeks period, the patients' periodontitis healed and closed entirely, and they were completely cured, returning their initial wound to its original healthy state.

EXAMPLE X

The exemplary antibacterial periodontal composition of Example VIII is prepared by mixing the following components: the oxidant (4 mL) and healing factors (1.5 mL) were mixed and combined with the photoactivators (1 mL). The resulting composition is pre-lliuminated with actinic light provided by a LED photocuring device (blue light), for less than 5 minutes before application to the mouth of a patient. After application, the composition is left in the mouth for less than 5 minutes. The composition was removed following treatment.

EXAMPLE XI

Dental Socket Closure

Figure 5A:
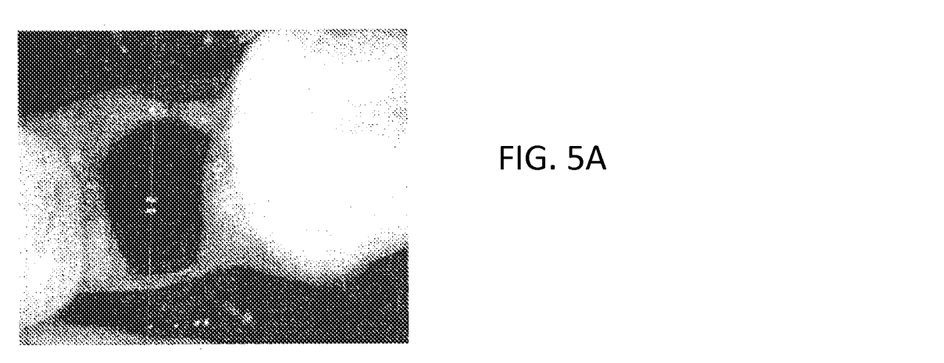
FIG. 5A is a picture illustrating a dental socket from which a tooth has been extracted.
Figure 5B:
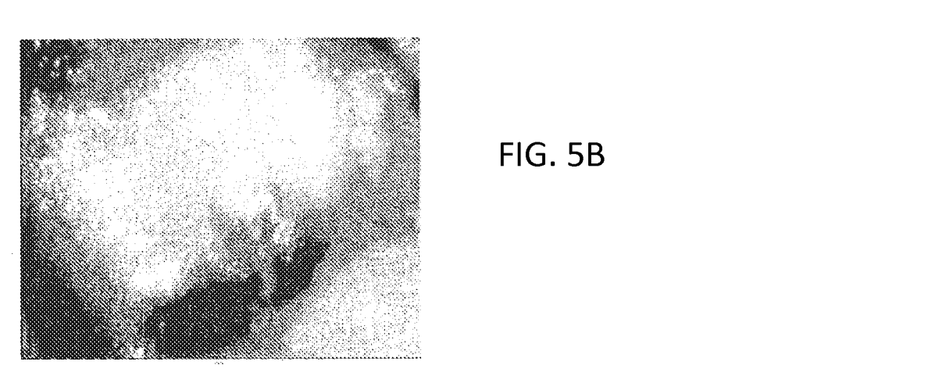
FIG. 5B is a picture illustrating the dental socket during treatment with a composition in accordance with an embodiment of the method of the present invention.
Figure 5C:
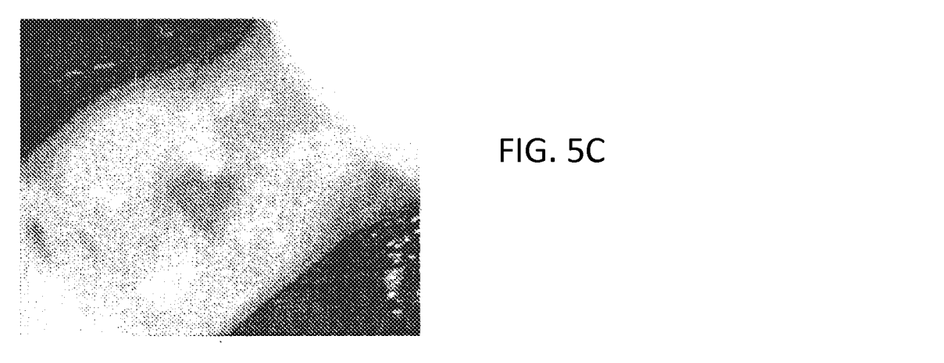
FIG. 5C is a picture of the dental pocket 24 hours after treatment with the composition in accordance with an embodiment method according to the present invention.

Now referring to FIG. 5, the tooth of a patient suffering from periodontitis, consecutive abscesses, loss of bone and increase mobility of the tooth, is extracted, leaving an open dental socket (FIG. 5A). The socket is cleaned and the antibacterial composition of Example VIII is applied to the socket (FIG. 5B), and exposed to actinic light for about 5 minutes. The antibacterial composition is then removed. 24 days after treatment, no blood clot is present, and newly formed tissue covers the socket (FIG. 5C). No suture is required to favor healing. Such accelerated healing does not generally occur following such teeth extraction.

The clinical observations from these results can be summarised as follows:

The gel application at the initial examination and supragingival scaling emulsifies and disperses the formation of the biofilm facilitating the easy removal and stains. It also facilitates the removal of hard deposits. The assumption to support the easy removal of the hard deposits is the protein breakdown by urea an organic compound with the chemical formula $(NH_2)_2CO$ which is released upon breakdown.

The release of $O_2$ causes mechanical disruption of the increments attached on the root surface, as well as a hyperaemia on the gingival soft tissues especially on the pocket epithelium conferring a light anaesthesia effect thereby diminishing the need of local anaesthesia during scaling/root planing. This further diminished the number of sessions demanded for the full mouth disinfection subgingival debridement.

The haemostatic effect of the $O_2$ release offers a clear operation field during subgingival debridement. Patients in the test group showed a great compliance due to the favourable effects of the gel as mentioned above. Last but not least during the photodynamic therapy a strong bactericidal effect takes place. By photo activating the gel which is in contact with the targeted tissues, a photochemical reaction takes place that accelerates the re-activity of the gel in the synergistic interaction of the three components light-tissues-gel. This interaction consequently increases the generation of oxygen reactive species (hydrogen peroxide, superoxide ion, singlet oxygen) and in the end of the chain, formation of molecular oxygen (bubbles). In addition, release of urea compound and formation of water are observed. The photosensitizers not only induce energy in the system via electron flow (that increases reactivity to the peroxide), but also direct the light energy to the biofilm, since they bind both to the biofilm itself and to haemoglobin. The impact of the free radicals release and the corresponding radical cascades on the biological substrate and the bacterial behaviour are known. These moderate bio-stimuli are lethal to the bacterial growth and the complexity of the mature biofilms.

The biostimulation of the living multicellular tissues; the bio-active selectivity of the co-interaction (light-tissues-gel), the light itself (bactericidal and hyperhaemic effect) and last but not least the micro-mechanical effect of molecular oxygen especially in closed milieu of the periodontal pocket, is something that should be emphasized and further investigated. This application of the gel is very helpful in facilitating supra and subgingival debridement apart from the bactericidal effect due to the photodynamic therapy.

While preferred embodiments of the invention have been described above and illustrated in the accompanying drawings, it will be evident to those skilled in the art that modifications may be made therein without departing from the essence of this invention. Such modifications are considered as possible variants comprised in the scope of the invention.

The invention claimed is:

1. A method of treating an oral disease, comprising:
   a) applying on a patient's oral tissue an effective amount of a composition comprising at least one oxidant, wherein the oxidant comprises about 3% to about 16% urea peroxide or about 1% to about 12% hydrogen peroxide; and a fluorescent compound; and
   b) exposing said composition to actinic light having an emission wavelength between about 400 nm and 700 nm for a time sufficient to cause a change in color of the fluorescent compound.

2. The method according to claim 1, wherein said oral disease is selected from gingivitis, periodontitis, periodontal disease, oral thrush, lichen planus, stomatitis, herpes simplex lesion, oral mucositis, oral ulcers, oral submucous fibrosis, and glossitis.

3. The method according to claim 1, wherein said composition is exposed to actinic light for a period of less than about 5 minutes.

4. The method according to claim 1, wherein said composition is exposed to actinic light for a period of about 60 seconds to about 5 minutes.

5. The method according to claim 1, wherein said composition is exposed to actinic light for a period of less than about 5 minutes per $cm^2$ of an area to be treated.

6. The method according to claim 1, wherein said composition is exposed to actinic light for a period of about 60 seconds to about 5 minutes per $cm^2$ of an area to be treated.

7. The method according to claim 1, wherein said oral tissue comprises a gingiva or a portion thereof.

8. The method according to claim 1, wherein said oral tissue is on or near at least one tooth.

9. The method according to claim 8, wherein said oral tissue that is on or near at least one tooth is exposed to actinic light for a period of about at least 10 seconds on a vestibular side, and of about at least 10 seconds on a oral side.

10. The method according to claim 1, wherein the oxidant comprises about 1% to about 12% hydrogen peroxide.

11. The method according to claim 1, wherein the oxidant comprises about 3% to about 16% urea peroxide.

12. The method according to claim 1, wherein the composition further comprises at least one hydrophilic gelling agent.

13. The method according to claim 1, wherein the hydrophilic gelling agent is selected from glucose, modified starch, methyl cellulose, carboxymethyl cellulose, propyl cellulose, hydroxypropyl cellulose, carbomer polymers, alginic acid, sodium alginate, potassium alginate, ammonium alginate, calcium alginate, agar, carrageenan, locust bean gum, pectin, and gelatin.

14. The method according to claim 1, wherein the fluorescent compound is Eosin Y.

15. The method according to claim 1, wherein the fluorescent compound is selected from a xanthene derivative dye, an azo dye, a biological stain and a carotenoid.

16. The method according to claim 1, wherein the composition further comprises at least one of: rhodamine B, rhodamine WT, rhodamine G, phloxine B, rose bengal, merbromine, eosin B, fluorescein, erythrosine B, saffranin O, saffron red powder, annatto extract, brown algae extract, basic fuchsin, acid fuschin, 3,3' dihexylocarbocyanine iodide, carminic acid, indocyanine green, crocetin, α-crocin (8,8-diapo-8,8-carotenoic acid), zeaxanthine, lycopene, α-carotene, β-carotene, bixin, fucoxanthine, methyl violet, neutral red, para red, amaranth, carmoisine, allura red AC, tartrazine, orange G, ponceau 4R, methyl red, murexide-ammonium purpurate, pyronine Y and pyronine B.

17. The method of claim 1, wherein the composition is applied prior to a supragingival debridement, a scaling/root planing, or both.

18. The method of claim 1, wherein the wound is exposed to the actinic light at least two, three, four, five or six times, and wherein a fresh application of the composition is applied before exposure to the actinic light.

19. The method of claim 1, wherein the composition further comprises a healing factor selected from glucosamine, allantoin and hyaluronic acid.

20. The method of claim 1, wherein the actinic light is emitted from a halogen lamp, an LED, or a plasma arc lamp.

* * * * *